(12) United States Patent
Peters et al.

(10) Patent No.: US 9,561,375 B2
(45) Date of Patent: *Feb. 7, 2017

(54) SYNCHRONIZATION CONTROL SYSTEM

(71) Applicant: Sunshine Heart Company Pty Ltd., Clontarf, NSW (AU)

(72) Inventors: William Suttle Peters, Auckland (NZ); Rodney Gordon Parkin, Crows Nest (AU)

(73) Assignee: Sunshine Heart Company Pty, Ltd., New South Wales (AU)

( * ) Notice: Subject to any disclaimer, the term of this patent is extended or adjusted under 35 U.S.C. 154(b) by 0 days.

This patent is subject to a terminal disclaimer.

(21) Appl. No.: 14/809,986

(22) Filed: Jul. 27, 2015

(65) Prior Publication Data

US 2015/0328466 A1    Nov. 19, 2015

Related U.S. Application Data

(63) Continuation of application No. 14/060,854, filed on Oct. 23, 2013, now Pat. No. 9,119,908, which is a
(Continued)

(30) Foreign Application Priority Data

Oct. 31, 2003    (AU) .................................. 2003906070

(51) Int. Cl.
*A61N 1/00*    (2006.01)
*A61N 1/365*    (2006.01)
(Continued)

(52) U.S. Cl.
CPC ......... *A61N 1/36578* (2013.01); *A61B 5/0006* (2013.01); *A61B 5/0408* (2013.01);
(Continued)

(58) Field of Classification Search
CPC . A61B 5/0006; A61B 5/04012; A61B 5/0408; A61B 5/0456; A61B 5/4836; A61B 7/00; A61M 1/106; A61M 1/107; A61M 1/1086; A61M 1/122; A61N 1/36514; A61N 1/36528; A61N 1/36578; A61N 1/37; A61N 1/3702

See application file for complete search history.

(56) References Cited

U.S. PATENT DOCUMENTS

| 283,660 A | 8/1883 | Reed |
| 929,571 A | 7/1909 | Dubied |

(Continued)

FOREIGN PATENT DOCUMENTS

| AU | 2003277983 | 6/2008 |
| DE | 1541311 | 9/1969 |

(Continued)

OTHER PUBLICATIONS

Hemodynamic and Metabolic Effects of Para- versus Intraaortic Counterpulsatile Circulation Supports.
(Continued)

*Primary Examiner* — George Manuel
(74) *Attorney, Agent, or Firm* — Schwegman Lundberg & Woessner, P.A.

(57) ABSTRACT

The various embodiments herein relate to systems and methods for controlling the operation of a pulsatile heart assist device in a patient. The systems and methods include utilizing sounds and electrical signals produced by the heart to control the operation of the heart assist device.

18 Claims, 4 Drawing Sheets

Related U.S. Application Data continuation of application No. 12/819,640, filed on Jun. 21, 2010, now Pat. No. 8,571,658, which is a continuation of application No. 10/595,601, filed as application No. PCT/AU2004/001486 on Oct. 28, 2004, now Pat. No. 7,765,003.

(51) Int. Cl.

| | | |
|---|---|---|
| *A61B 5/0456* | (2006.01) | |
| *A61M 1/12* | (2006.01) | |
| *A61M 1/10* | (2006.01) | |
| *A61N 1/37* | (2006.01) | |
| *A61B 5/00* | (2006.01) | |
| *A61B 5/04* | (2006.01) | |
| *A61B 5/0408* | (2006.01) | |
| *A61B 7/00* | (2006.01) | |

(52) U.S. Cl.
CPC ........ *A61B 5/04012* (2013.01); *A61B 5/0456* (2013.01); *A61B 5/4836* (2013.01); *A61B 7/00* (2013.01); *A61M 1/106* (2013.01); *A61M 1/107* (2013.01); *A61M 1/1086* (2013.01); *A61M 1/122* (2014.02); *A61N 1/36514* (2013.01); *A61N 1/3702* (2013.01); *A61N 1/36528* (2013.01)

(56) References Cited

U.S. PATENT DOCUMENTS

| | | |
|---|---|---|
| 1,576,397 A | 7/1925 | Yanagi |
| 1,719,316 A | 7/1929 | Appleton |
| 3,467,077 A | 9/1969 | Cohen |
| 3,552,383 A | 1/1971 | Krueger et al. |
| 3,597,766 A | 8/1971 | Buck |
| 4,014,318 A | 3/1977 | Dockum et al. |
| 4,051,840 A | 10/1977 | Kantrowitz et al. |
| 4,176,411 A | 12/1979 | Runge |
| 4,195,623 A | 4/1980 | Zeff et al. |
| 4,236,482 A | 12/1980 | Gingerich et al. |
| 4,256,094 A | 3/1981 | Kapp |
| 4,277,706 A | 7/1981 | Issacson |
| 4,304,225 A | 12/1981 | Freeman |
| 4,454,891 A | 6/1984 | Dreibelbis et al. |
| 4,457,673 A | 7/1984 | Conley et al. |
| 4,459,977 A | 7/1984 | Pizon et al. |
| 4,515,587 A | 5/1985 | Schiff |
| 4,583,523 A | 4/1986 | Kleinke et al. |
| 4,594,731 A | 6/1986 | Lewkowicz |
| 4,630,597 A | 12/1986 | Kantrowitz et al. |
| 4,676,482 A | 6/1987 | Reece et al. |
| 4,697,574 A | 10/1987 | Karcher et al. |
| 4,737,083 A | 4/1988 | Meyer |
| 4,763,646 A | 8/1988 | Lekholm |
| 4,771,765 A | 9/1988 | Choy et al. |
| 4,809,676 A | 3/1989 | Freeman |
| 4,813,952 A | 3/1989 | Khalafalla |
| 4,822,357 A | 4/1989 | Forster et al. |
| 4,881,939 A | 11/1989 | Newman |
| 4,925,443 A | 5/1990 | Heilman et al. |
| 4,957,477 A | 9/1990 | Lundback |
| 4,979,936 A | 12/1990 | Stephenson et al. |
| 5,089,017 A | 2/1992 | Young et al. |
| 5,169,378 A | 12/1992 | Figuera |
| 5,197,980 A | 3/1993 | Gorahkov et al. |
| 5,205,810 A | 4/1993 | Guiraudon et al. |
| 5,222,980 A | 6/1993 | Gealow |
| 5,267,940 A | 12/1993 | Moulder |
| 5,273,518 A | 12/1993 | Lee |
| 5,290,249 A | 3/1994 | Foster et al. |
| 5,300,111 A | 4/1994 | Panton et al. |
| 5,337,752 A | 8/1994 | Reeves |
| 5,344,385 A | 9/1994 | Buck et al. |
| 5,346,458 A | 9/1994 | Affeld |
| 5,360,445 A | 11/1994 | Goldowsky |
| 5,372,573 A | 12/1994 | Habib |
| 5,383,915 A | 1/1995 | Adams |
| 5,429,584 A | 7/1995 | Chiu |
| 5,447,523 A | 9/1995 | Schaldach |
| 5,453,076 A | 9/1995 | Kiyota et al. |
| 5,511,551 A | 4/1996 | Sano et al. |
| 5,554,177 A | 9/1996 | Kieval et al. |
| 5,569,156 A | 10/1996 | Mussivand |
| 5,593,414 A | 1/1997 | Shipp et al. |
| 5,607,378 A | 3/1997 | Winston |
| 5,647,380 A | 7/1997 | Campbell et al. |
| 5,702,427 A * | 12/1997 | Ecker ................ A61N 1/36542 607/28 |
| 5,722,930 A | 3/1998 | Larson, Jr. et al. |
| 5,792,195 A | 8/1998 | Carlson et al. |
| 5,814,012 A | 9/1998 | Fleenor et al. |
| 5,820,542 A | 10/1998 | Dobak, III et al. |
| 5,827,171 A | 10/1998 | Dobak, III et al. |
| 5,833,655 A | 11/1998 | Freed et al. |
| 5,843,170 A | 12/1998 | Ahn |
| 5,876,434 A | 3/1999 | Flomenblit |
| 5,975,140 A | 11/1999 | Lin |
| 5,980,448 A | 11/1999 | Heilman et al. |
| 6,030,336 A | 2/2000 | Franchi |
| 6,030,366 A | 2/2000 | Mitchell |
| 6,045,496 A | 4/2000 | Pacella et al. |
| 6,066,085 A | 5/2000 | Heilman et al. |
| 6,132,363 A | 10/2000 | Freed et al. |
| 6,132,636 A | 10/2000 | Singh et al. |
| 6,146,325 A | 11/2000 | Lewis et al. |
| 6,210,318 B1 | 4/2001 | Lederman |
| 6,210,319 B1 | 4/2001 | Williams et al. |
| 6,226,843 B1 | 5/2001 | Crainich |
| 6,251,061 B1 | 6/2001 | Hastings et al. |
| 6,406,422 B1 | 6/2002 | Landesberg |
| 6,432,039 B1 | 8/2002 | Wardle |
| 6,471,633 B1 | 10/2002 | Freed |
| 6,553,263 B1 | 4/2003 | Meadows et al. |
| 6,572,534 B1 | 6/2003 | Milbocker et al. |
| 6,585,635 B1 | 7/2003 | Aldrich |
| 6,616,596 B1 | 9/2003 | Milbocker |
| 6,626,821 B1 | 9/2003 | Kung et al. |
| 6,643,548 B1 | 11/2003 | Mai et al. |
| 6,808,483 B1 | 10/2004 | Ortiz et al. |
| 6,808,484 B1 | 10/2004 | Peters et al. |
| 6,984,201 B2 | 1/2006 | Khaghani et al. |
| 7,169,109 B2 | 1/2007 | Jansen et al. |
| 7,306,558 B2 | 12/2007 | Peters et al. |
| 7,347,811 B2 | 3/2008 | Peters et al. |
| 7,357,771 B2 | 4/2008 | Peters et al. |
| 7,513,864 B2 | 4/2009 | Kantrowitz et al. |
| 7,616,990 B2 | 11/2009 | Chavan et al. |
| 7,738,965 B2 | 6/2010 | Phillips et al. |
| 7,740,575 B2 | 6/2010 | Peters et al. |
| 7,765,003 B2 | 7/2010 | Peters et al. |
| 8,002,691 B2 | 8/2011 | Peters et al. |
| 2001/0016676 A1 | 8/2001 | Williams et al. |
| 2003/0078634 A1 | 4/2003 | Schulman et al. |
| 2003/0105497 A1 | 6/2003 | Zhu et al. |
| 2003/0233023 A1 | 12/2003 | Khaghani et al. |
| 2004/0010180 A1 | 1/2004 | Scorvo |
| 2004/0073080 A1 | 4/2004 | Peters et al. |
| 2004/0097783 A1 | 5/2004 | Peters et al. |
| 2004/0097784 A1 | 5/2004 | Peters et al. |
| 2004/0147803 A1 | 7/2004 | Hegde et al. |
| 2004/0152945 A1 | 8/2004 | Kantrowitz et al. |
| 2005/0267323 A1 | 12/2005 | Dorros et al. |
| 2006/0052866 A1 | 3/2006 | Gilles et al. |
| 2006/0085039 A1 | 4/2006 | Hastings et al. |
| 2007/0021830 A1 | 1/2007 | Peters |
| 2007/0060787 A1 | 3/2007 | Peters et al. |
| 2007/0093684 A1 | 4/2007 | Peters et al. |
| 2007/0129796 A1 | 6/2007 | Miller |
| 2007/0135677 A1 | 6/2007 | Miller et al. |
| 2007/0167898 A1 | 7/2007 | Peters et al. |
| 2007/0255350 A1 | 11/2007 | Torgerson |
| 2008/0027270 A1 | 1/2008 | Peters et al. |
| 2008/0139873 A1 | 6/2008 | Peters et al. |

(56) References Cited

U.S. PATENT DOCUMENTS

| | | |
|---|---|---|
| 2008/0161795 A1 | 7/2008 | Wang et al. |
| 2008/0167515 A1 | 7/2008 | Peters et al. |
| 2008/0194905 A1 | 8/2008 | Walsh |
| 2008/0266748 A1 | 10/2008 | Lee |
| 2009/0054949 A1 | 2/2009 | Alexander et al. |
| 2009/0118826 A1 | 5/2009 | Khaghani |
| 2009/0149950 A1 | 6/2009 | Wampler |
| 2009/0204170 A1 | 8/2009 | Hastings et al. |
| 2009/0276016 A1 | 11/2009 | Phillips et al. |
| 2010/0016835 A1 | 1/2010 | Davey |
| 2010/0070019 A1 | 3/2010 | Shalev |
| 2010/0191036 A1 | 7/2010 | Sullivan |
| 2010/0256440 A1 | 10/2010 | Maher |
| 2010/0292528 A1 | 11/2010 | De Plater |
| 2010/0292629 A1 | 11/2010 | Dacey, Jr. et al. |
| 2010/0298625 A1 | 11/2010 | Reichenbach et al. |
| 2010/0324354 A1 | 12/2010 | Peters |
| 2011/0166630 A1 | 7/2011 | Phillips et al. |
| 2011/0270331 A1 | 11/2011 | Peters et al. |
| 2011/0275883 A1 | 11/2011 | Peters |
| 2011/0288367 A1 | 11/2011 | Miller |
| 2011/0298304 A1 | 12/2011 | Cotter |
| 2011/0301668 A1 | 12/2011 | Forsell |
| 2012/0065457 A1 | 3/2012 | Peters et al. |
| 2012/0095280 A1 | 4/2012 | Timms |
| 2012/0305603 A1 | 12/2012 | Kwok et al. |
| 2014/0205434 A1 | 7/2014 | Graichen |

FOREIGN PATENT DOCUMENTS

| | | |
|---|---|---|
| EP | 0217964 | 4/1987 |
| EP | 0080348 B2 | 5/1988 |
| EP | 0363203 | 4/1990 |
| EP | 0364799 | 4/1990 |
| EP | 0216042 | 3/1991 |
| EP | 0601804 | 6/1994 |
| EP | 0583012 | 7/1996 |
| EP | 0547733 | 4/1998 |
| EP | 1129736 | 9/2001 |
| FR | 2458288 | 1/1981 |
| FR | 2645739 | 10/1990 |
| FR | 2767874 | 3/1999 |
| GB | 2422114 | 4/2008 |
| JP | H6-510461 | 11/1994 |
| JP | 9-502376 | 3/1997 |
| JP | 9-503933 | 4/1997 |
| JP | 10-328297 | 12/1998 |
| JP | 11285529 A | 10/1999 |
| JP | H11-285529 | 10/1999 |
| JP | 2000-000299 | 1/2000 |
| JP | 2000-510006 | 8/2000 |
| JP | 2001-276213 | 10/2001 |
| JP | 2003501180 A | 1/2003 |
| JP | 2003-135497 | 5/2003 |
| JP | 2015000723 A | 1/2015 |
| WO | WO 90/15630 | 12/1990 |
| WO | WO 92/08500 | 5/1992 |
| WO | WO 93/08874 | 5/1993 |
| WO | WO 95/05122 | 2/1995 |
| WO | WO 95/28127 | 10/1995 |
| WO | WO9624395 | 8/1996 |
| WO | WO 97/40755 | 11/1997 |
| WO | WO 98/05289 | 2/1998 |
| WO | WO 98/14239 | 4/1998 |
| WO | WO 98/51367 | 11/1998 |
| WO | WO 99/02213 | 1/1999 |
| WO | WO 99/04833 | 2/1999 |
| WO | WO 99/45981 | 9/1999 |
| WO | WO 00/12168 | 3/2000 |
| WO | WO 00/76288 | 12/2000 |
| WO | WO 0076288 A2 | 12/2000 |
| WO | WO 01/13974 | 3/2001 |
| WO | WO 01/83001 | 11/2001 |
| WO | WO 02/24254 | 3/2002 |
| WO | WO 02/24255 | 3/2002 |
| WO | WO 02/076305 | 10/2002 |
| WO | WO 03/011365 | 2/2003 |
| WO | WO 03/028787 | 4/2003 |
| WO | WO 2004037152 A2 | 5/2004 |
| WO | WO 2004/045677 | 6/2004 |
| WO | WO-2004078234 A2 | 9/2004 |
| WO | WO 2005/041783 | 5/2005 |
| WO | WO 2005/042063 | 5/2005 |
| WO | WO 2005/042089 | 5/2005 |
| WO | WO 2005/044338 | 5/2005 |
| WO | WO2005042089 A1 | 5/2005 |
| WO | WO 2005/110512 | 11/2005 |
| WO | WO 2008/053469 | 5/2008 |
| WO | WO 2008/071223 | 6/2008 |
| WO | WO2011056280 | 5/2011 |
| WO | WO 2011/098769 | 8/2011 |

OTHER PUBLICATIONS

Seymour Furman et al., "Cardiac Support by Periaortic Diastolic Augmentation", New York Journal of Medicine, Aug. 1, 1970, pp. 1964-1969.

J.L. Stewart, "Aortic Cuff a Cardiac Assistance Device", Polytechnic Institute of Brooklyn, 1968, pp. 9-108.

Hiroshi Odaguchi et al., "Experimental Study of Extraaortic Balloon Counterpulsation as a Bridge to Other Mechanical Assists" ASAIO Journal, pp. 190-194, vol. 42, No. 3, Lippincott Williams & Wilkins/ASAIO, Hagerstown, MD, May 1, 1996. cited by other.

"Use of Heart Valve Sounds as Input to Cardiac Assist Devices", Research Disclosures, Mar. 1995.

Luisada et al., On the Function of the Aortic Valve and the Mechanism of the First and Second Sounds, Japanese Heart Journal, vol. 18(1), Jan. 1977, pp. 81-91.

International Search Report issued in PCT/AU00/00654, mailed Aug. 18, 2000, 5 pages.

International Search Report issued in PCT/AU2002/000974, mailed Oct. 11, 2002, 5 pages.

International Preliminary Examination Report issued in PCT/AU2002/000974, completed Aug. 11, 2003, 8 pages.

International Search Report issued in PCT/AU2001/01187, mailed Nov. 5, 2001, 3 pages.

International Preliminary Examination Report issued in PCT/AU2001/01187, completed May 2, 2002, 4 pages.

International Search Report and Written Opinion issued in PCT/AU2007/001188, mailed Oct. 4, 2007, 12 pages.

International Preliminary Report on patentability, Chapter II, issued in PCT/AU2007/001188, completed Mar. 11, 2008, 8 pages.

International Search Report issued in PCT/AU2003/001450, mailed Feb. 2, 2004, 2 pages.

International Preliminary Examination Report issued in PCT/AU2003/001450, completed Mar. 2, 2005, 4 pages.

International Search Report issued in PCT/AU2003/001458, mailed Feb. 5, 2004, 5 pages.

International Prelminary Examination Report issued in PCT/AU2003/001458, completed Mar. 7, 2005, 7 pages.

International Search Report and Written Opinion issued in PCT/AU2004/001483, mailed Nov. 26, 2004, 5 pages.

International Search Report and Written Opinion issued in PCT/AU2004/001484, mailed Nov. 29, 2004, 5 pages.

International Search Report and Written Opinion issued in PCT/AU2004/01485, mailed Feb. 7, 2005, 6 pages.

International Search Report and Written Opinion issued in PCT/AU2004/001486, mailed Jan. 6, 2005, 7 pages.

International Search Report and Written Opinion issued in PCT/AU2004/01487, mailed Jan. 27, 2005, 12 pages.

International Search Report and Written Opinion issued in PCT/AU2004/01488, mailed Dec. 15, 2004, 6 pages.

Supplemental European Search Report issued in EP Application 00934813, mailed 0/19/2006, 2 pages.

Supplemental European Search Report issued in EP 01971489, completed Nov. 22, 2006, 4 pages.

Supplemental European Search Report issued in EP App No. 02748447, Feb. 6, 2007, 6 pages.

(56) References Cited

OTHER PUBLICATIONS

Supplemental European Search Report issued in EP App. No. 04789624, mailed Mar. 6, 2008, 7 pages.
Supplemental European Search Report issued in EP 04789625, mailed Nov. 18, 2009, 6 pages.
Office Action issued in JP Application No. 2004-552261, dated Mar. 2, 2010.
Office Action issued in JP Application No. 22006-53700, dispatched Jun. 22, 2010, with English translation, 12 pages.

* cited by examiner

SYNCHRONIZATION CONTROL SYSTEM

CROSS-REFERENCE TO RELATED APPLICATION(S)

This application claims priority as a continuation of U.S. patent application Ser. No. 14/060,854, filed on Oct. 23, 2013, which claims priority as a continuation of U.S. Pat. No. 8,571,658, filed on Jun. 21, 2010 and issued on Oct. 29, 2013, which claims priority as a continuation of U.S. Pat. No. 7,765,003, filed on Apr. 28, 2006 and issued on Jul. 27, 2010, which was the U.S. national stage filing of PCT Application PCT/AU2004/01486, filed on Oct. 28, 2004, which claims priority to Australian Provisional Patent Application No. 2003096070, filed on Oct. 21, 2003.

FIELD OF THE INVENTION

The present invention relates to methods and devices for controlling the operation of a pulsatile heart assist device or pacemaker.

BACKGROUND OF THE INVENTION

Counterpulsation heart assist devices must be controlled to operate in a predetermined time relationship with the pulsing of a patient's heart. For example, the counterpulsation heart assist devices disclosed in the Applicant's above noted PCT patent application are configured to compress the aorta in synchrony with the diastolic period, the beginning of which is marked by closure of the aortic valve (which produces an audible sound known as second heart sound, or S2) to reduce the interior volume of the aorta during diastole. This compression increases systemic blood pressure, increases blood flow through the coronary arteries and increases diastolic output against the closed aortic valve. The compression of the aorta is alternated with periodic withdrawal of aortic compression following the R wave of the ECG (indicating ventricular depolarisation), around the time, known as presystole, of the closing of the mitral and tricuspid valves (audibly, the first heart sound, or S1) and opening of the aortic valve (marking the beginning of systole) to allow the aorta to return to its normal interior volume. This withdrawal of compression of the aorta at the time the heart is first ejecting blood from the left ventricle unloads the heart so that it can eject blood from the left ventricle more easily. Timing of deflation of the device in relation to the R wave or the detected first heart sound (S1), and inflation in relation to the second heart sound (S2) may be varied according to specific patients' physiology.

It will be apparent to those skilled in the art that the extent of heart assistance provided by counter-pulsation heart assist devices depends upon accurately timing the compression and decompression of the aorta relative to the timing of the native heart. In embodiments of the invention which relate to co-pulsation of the heart, the timing of compression of the heart must be also timed to its native rhythm.

Current devices rely on the ECG, particularly the R wave, to time deflation of the cuff, and inflation of the cuff may be timed to the dichrotic notch of the aortic pressure tracing, which indicates aortic valve closure. This methodology is severely limited in its application for control of heart assist devices and the like for a number of reasons:

1. The ECG is good for indicating the beginning of ventricular contraction, but does not indicate the end of systole. Further, whilst the T-wave indicates ventricular repolarisation, it is broad-based and not very accurate for timing purposes;

2. The systemic arterial blood pressure is very good at highlighting the time of aortic valve closure, but is only useful in a temporary manner, via a percutaneous arterial line, and is not suitable for long-term use;

3. The arterial pressure wave form is coupled to, but delayed, the more further peripherally the arterial pressure is measured from the aortic valve, and may not accurately describe the time of closure of the aortic valve; and 4. As the heart rate varies (particularly if the patient is suddenly exercising, or anxious, or the rhythm is in atrial fibrillation, or depending on the contractile state of the myocardium etc), time of opening and closure of the aortic valve after the R-wave of the ECG may vary significantly, thus whilst the beginning of systole can be relatively safely timed (and balloon deflation initiated), the timing of the beginning of diastole is not possible with ECG alone.

There is no reliable and accurate way to determine particularly the timing of aortic valve closure long-term in manner that allows patients to enjoy a good life-style whilst fitted with the device.

Methods are disclosed in U.S. Pat. Nos. 5,904,666 and 6,042,532, assigned to L. Vad Technology, Inc., to transduce the aortic pressure wave form every two to three minutes by taking a measurement of the dichrotic notch of the aortic blood pressure tracing. However, this requires the device functionality to be paused every 2-3 minutes to male measurements. This does not allow precise control of device function to specific heart beats, rather, timings are set for 2 minutes, until the measurement is re-done. Further, the dichrotic notch may not always be detected.

Another problem associated with components used to control partially implantable heart assist devices (i.e. having external drivers/controllers) is that the size, number, and rigidity of any percutaneous tubing or wires must be kept to a minimum to reduce the chance of infection and increase psychological acceptance of the devices. This can be achieved by the use of wireless transmission of cardiac cycle timing signals. However, the wireless telemetry associated with pacemakers is usually proprietary and unnecessarily complex, and is not suited for continuous discreet signal outputs It is an object of the present invention to provide methods and devices for determining and adjusting counterpulsation inflation timing by using detected heart sounds. In preferred embodiments, the heart sounds are monitored real-time to cause accurate beat-to-beat counterpulsation timing for each specific cardiac cycle, without interruption of heart assist functionality. Heart sounds may also be used intermittently to determine and reset the interval between R wave balloon deflation or inflation, either at fixed time intervals, or when there is a sustained change in the heart rate.

Another object is to provide, again at least in preferred embodiments, simple and economical wireless telemetry of the detected signals to an external device.

BRIEF SUMMARY

In a first aspect, the present invention provides a method of controlling the operation of a pulsatile heart assist device in a patient, consisting of utilising sounds produced by the heart to control the operation of the heart assist device.

Preferably, the method uses a combination of R-wave detection and heart sound detection to control the operation of the heart assist device. Alternatively, the heart assist device may be completely controlled by utilising both the S1 and S2 sounds of the heart to both stop and start the heart assist device.

In a second aspect, the present invention provides a method of controlling the operation of a pulsatile heart assist device in a patient, consisting of electrically detecting the R-wave of the patient's heart rhythm and producing a signal to initiate a change in the pulsatile status of the heart assist device, and detecting a sound or pressure wave created by the closure of the patient's aortic valve and producing a signal to return the heart assist device to the pulsatile status it had before the preceding R-wave.

In a third aspect, the present invention provides a method of controlling the operation of a pulsatile heart assist device with a multi-channel digital signal processor and transmitter (DSPT), the DSPT being of the type having an ECG channel and a phonocardiographic (PCG) channel, the DSPT being at least adapted to normally sense an electrical signal indicative of cardiac rhythm through the ECG channel, and to normally sense heart sounds through the PCG channel, and to transmit signals to an external receiver, the method comprising the steps of operatively connecting the DSPT bipolar ECG lead to a patient's heart; and operatively connecting the DSPT microphone to the patient's heart, whereby, after detecting an R-wave via the ECG channel, the DSPT issues a R-wave signal to the heart assist device controller to control the timing of the pulsation of the heart assist device, and whereby, after detecting a heart sound via the PCG channel, the DSPT issues a heart sound signal to the heart assist device controller to control the timing of the pulsation of the heart assist device.

The DSPT is preferably adapted to normally sense heart sounds through the PCG channel in the range of 20-500 Hz.

The DSPT is preferably able to receive as well as transmit, more preferably the DSPT has parameter settings adjusted within ranges, for detecting the R-wave and the heart sounds, and for the output signals.

The ECG lead connected to the patient's heart can be epicardial or endocardial or attached to an implanted heart assist device itself. In another embodiment sensors for the collection of an ECG signal may be embedded into the surface of a heart assist device applied to the heart or another part of the patient's body from which an ECG signal may be received.

The DSPT microphone may be internal to the patient's body. In this case connection to the patient's heart can be epicardial or endocardial, in the manner of a pacing lead, or attached to the implanted device itself, and, in this embodiment, is preferably located within 50 mm of the cardiac valves, and more preferably without the lung between the microphone and the patient's heart.

Alternatively the microphone may be positioned outside the body of the patient. The heart sounds and ECG to control an external gas-driven extra-aortic balloon pump may use an external microphone placed in the lumen of the extra aortic balloon or the gas line leading to it. The implanted gas line and balloon acts as a very efficient 'stethoscope', and heart sounds can be detected intermittently or continuously, and sent directly to a controller positioned outside the patient's body. Similarly, rather than requiring an implanted signal processor and transmitter, a percutaneous ECG lead may be used to directly transmit the ECG signal to the controller. The ECG lead may be combined with the percutaneous gas line or can be separate from the gas line. In either embodiment, it is preferable that there is a releasable and sealable connection for gas line and ECG lead under the skin, so that in the event of infection or non-use, the percutaneous lines can be removed, whilst leaving the gas line and ECG lead implanted for latter re-connection if required.

The DSPT is preferably also able to receive signals from an external device to adjust digital signal processing variables within the DSPT for detecting R-wave and heart sounds.

Preferably the DSPT has a battery of sufficient life that the DSPT can be removed and replaced, independent of the cardiac sensing leads, or that the DSPT has a rechargeable battery that can be recharged by induction, or Transcutaneous Energy Transfer (TET).

Further, the DSPT may communicate directly with an implanted controller, such as is contemplated with an implanted electrohydraulic Extra Aortic Balloon Pump (EABi)—the controller and the ECG and microphone may all be contained within the pump to limit the need for any leads, and the pump positioned, as intended, in the medial right chest, with one aspect of the pump (containing hermetically sealed microphone and ECG electrodes) against the right heart structures In a fourth aspect, the present invention provides a dual channel DSPT configured for use in controlling the operation of a pulsatile heart assist device, the DSPT being of the type having an ECG channel and a phonocardiographic (PCG) channel, the DSPT being at least adapted to normally sense an electrical signal indicative of cardiac rhythm through the ECG channel, and to normally sense heart sounds through the PCG channel, and to transmit signals to an external receiver to control the timing of the pulsation of the heart assist device. Signals may alternatively be directly sent to an implanted controller.

The DSPT is preferably adapted to normally sense heart sounds through the PCG channel in the range of 20-500 Hz.

The DSPT is preferably able to receive as well as transmit. More preferably, the DSPT has parameter settings adjustable within ranges, for detecting the R-wave and the Heart Sounds, and for the output signals.

The DSPT may have other channels for detecting aortic and left ventricular blood pressure and for movement of the aortic or ventricular walls, and signals from these channels may also be interpreted to control heart assist device functioning.

The heart assist device may be a co-pulsation device (such as an LVAD or a cardiac compression device) in which case the pulsations are in synchrony with the heart's native rhythm or it may be a counter-pulsation device in which the pulsations are out of phase with the heart's native rhythm. In the former configuration, the heart assist device may be of the type applying pulsatile compression of the heart itself. In the latter configuration, the heart assist device may be of the type adapted to apply pulsatile compression to a blood vessel either by compression of the outside of the vessels or by causing an intra-luminal device to expand and thereby cause blood volume displacement and pressure change in the systemic arterial system.

In a fifth aspect, the present invention provides means for controlling a co-pulsation or counter-pulsation heart assist device, the means including:

a co- or counter-pulsation heart assist device;

a controller for the heart assist device; and a DSPT of the type at least adapted to normally sense an electrical signal indicative of cardiac rhythm through an ECG channel and a sound signal indicative of heart sounds S1 and/or S2 through a PCG channel, and to issue identifiable signals to the controller, in which the DSPT is set to issue pacing signals from the ventricular circuit at a minimum rate which is below a physiologically sensible rate in the event that the atrial circuit is unable to sense a rhythm signal from the patient's ventricle, and the controller is set to turn off the heart assist device in the event that the pacing signals that the controller receives from the DSPT are at a rate below a predetermined rate which is above the minimum rate.

By adopting this approach if the controller is not sensing any signals at all it may mean that the controller has become disconnected from the DSPT or that the DSPT or the controller has run out of battery. As the latter condition can usually be detected readily, and in advance, the cause of the lack of signals can usually be rapidly identified. Alternatively if the signals fall to the minimum rate, at which time the device will have stopped, it can indicate there is a fault condition present in the pacing lead or the pacemaker or that the patient has died.

This rapid isolation of the cause of malfunction can assist in rapidly correcting the condition causing the malfunction. In the case of a patient dying it will prevent the heart assist device continuing to operate after death.

The DSPT is preferably adapted to normally sense heart sounds through the PCG channel in the range of 20-500 Hz.

The DSPT is preferably able to receive as well as transmit, more preferably the DSPT has parameter settings adjustable within ranges, for detecting the R-wave and the Heart Sounds, and for the output signals.

The method preferably includes implanting the DSPT under the skin in front of the shoulder in the delto-pectoral region or over the abdomen

BRIEF DESCRIPTION OF THE DRAWINGS

Preferred forms of the present invention will now be described, by way of examples only, with reference to the accompanying drawings, wherein.

DETAILED DESCRIPTION

By way of further background, the DSPT has the basic modalities of sensing, transmitting, and programmability.

Sensing is the capability to detect and interpret a patient's native heart electro- and phonocardiograms (ECG's and PCG's respectively). An implanted sensing lead detects the patient's native heart electrical activity and transmits it to the DSPT circuitry. The firmware and/or software within the DSPT unit interprets the patient's R-wave detection. An implanted microphone lead detects the patient's native heart sounds and transmits it to the DSPT circuitry. The firmware and/or software within the DSPT unit interprets the patient's heart sounds and transmits a signal indicating S1 and S2 detection.

Programmability is the capability to allow a physician to adjust the DSPT's sensing and transmitting functions to the patient's individual needs. This is achieved by using a laptop-like device, typically called a programmer, that has an input device that is placed over the patient's skin in the vicinity of an implanted DSPT. The programmer transdermally communicates with the patient's DSPT, using either auditory (tonal) or electromagnetic pulses, and allows the physician to manipulate the DSPTs settings as needed.

The ECG sensing system is expected to be able to work in the presence of a dual-chambered pacemaker providing pacing control over the patient's rhythm because their native rhythm would be deficient or absent.

Combination pacemakers and internal cardioverter/defibrillators (ICDs) can, when ventricular tachycardia or VF is sensed, either attempt to "overdrive" pace a patient out of the rhythm (i.e. pace with a strong impulse that will override the patient's native rhythm and slowly decrease rate to control the patient's rhythm) or shock the heart out of the rhythm and then pace it.

Figure 1:
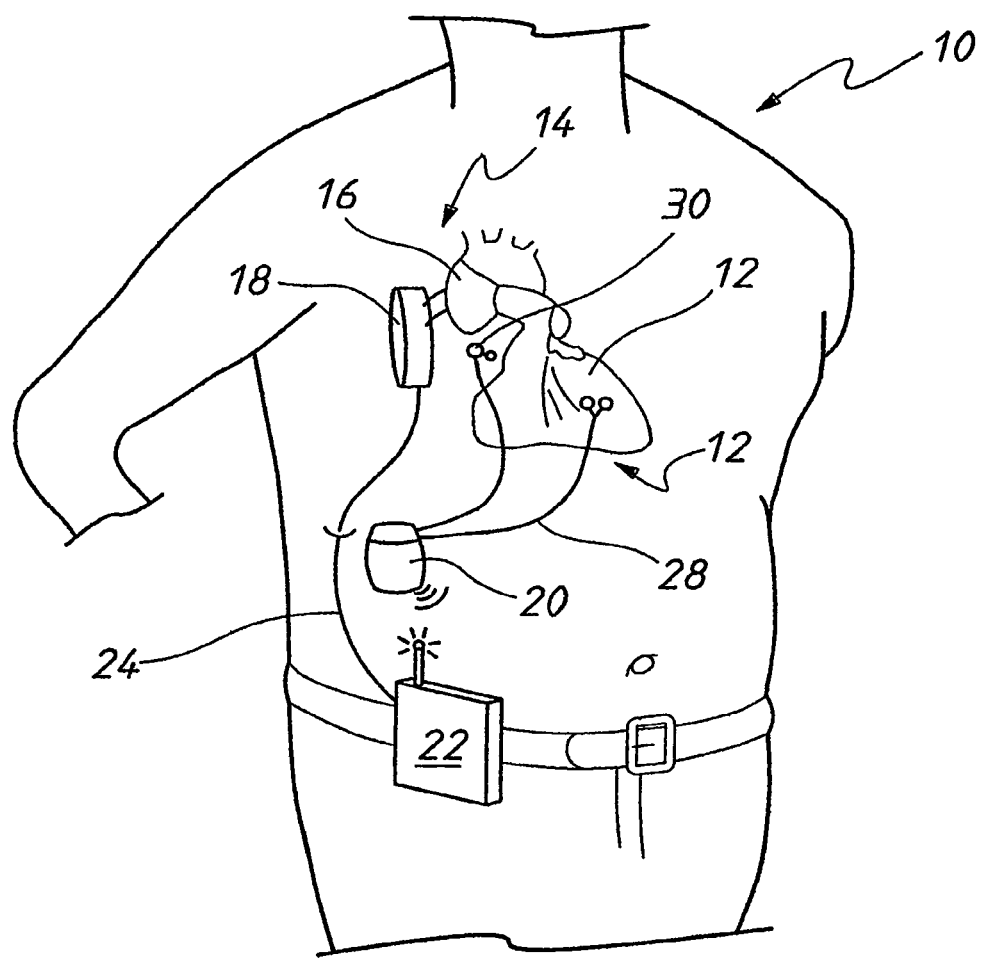
FIG. 1 is a cut away view of a patient with a heart assist device controlled in accordance with a first embodiment of the invention.

A first embodiment of the invention will now be described with reference to FIG. 1, which shows a patient 10 with a heart 12. The output of the heart 12 is assisted by a pulsatile, fully implantable, heart assist device, indicated generally by the reference numeral 14. The heart assist device 14 has an aortic cuff 16 around the patient's ascending aorta. The cuff 16 is essentially the same as those disclosed in the Applicant's previously referred to International PCT Patent application no. PCT/AU00/00654. The cuff 16 is driven by a pump 18, which essentially the same as those disclosed in the Applicant's International PCT Patent application no. PCT/AU02/00974 entitled "A fluid pressure generating means". Also shown is an implanted DSPT 20. The pump 18 is powered/controlled by an external battery/controller 22 via a percutaneous electrical cable 24. The DSPT 20 transmits RF signals to the controller 22 of the heart assist device 14.

The DSPT 20 has an ECG channel connected to sensing lead 26 and an PCG channel connected to the microphone lead 28.

The DSPT ECG channel is connected, via the sensing lead 26, to the epicardial surface of the ventricle of the patient's heart 12 and the DSPT PCG channel is connected, via the microphone lead 28, to a microphone 30 implanted in close proximity to the aortic valve, exterior to the aortic root In operation, the DSPT 20 detects an R-wave (i.e. the R wave of the ventricle) through the ECG channel, then waits for a predetermined time (for example from 0-30 msec) before transmitting a signal to the controller 22 which in turn controls the pulsation of the heart assist device 14. It will be understood that, in the above configuration, the DSPT 20 will always issue the signal to the controller 22 and the controller may be programmable as to what action is taken when this signal is received. If desired, the DSPT 20 may issue the signal from the ECG channel immediately upon receiving the sensed signal in the ECG channel. In this case there would be a variable delay programmable into the controller 22 to ensure that the time at which the heart assist device 14 is actuated is correctly timed for that individual patient.

Further, the DSPT 20 is designed to allow correct sensing of cardiac activity even in the presence of electrical or pressure or other noise interference. It is also designed to withstand defibrillation pulses without damage.

In the preferred form shown, the heart assist device 14 is a counter pulsation device in which the pulsations are out of phase with the heart's native rhythm.

The controller 22 is configured to turn the heart assist device off in the event that the pacing signal received from the ventricular circuit falls below a rate below the minimum rate, say 40 beats per minute. If the controller 22 indicates that it is not receiving any pacing signal this will be typically indicative of the DSPT 20 not transmitting to the controller 22 or a gross malfunction of the DSPT 20 or its leads 26 or 28.

Figure 2:
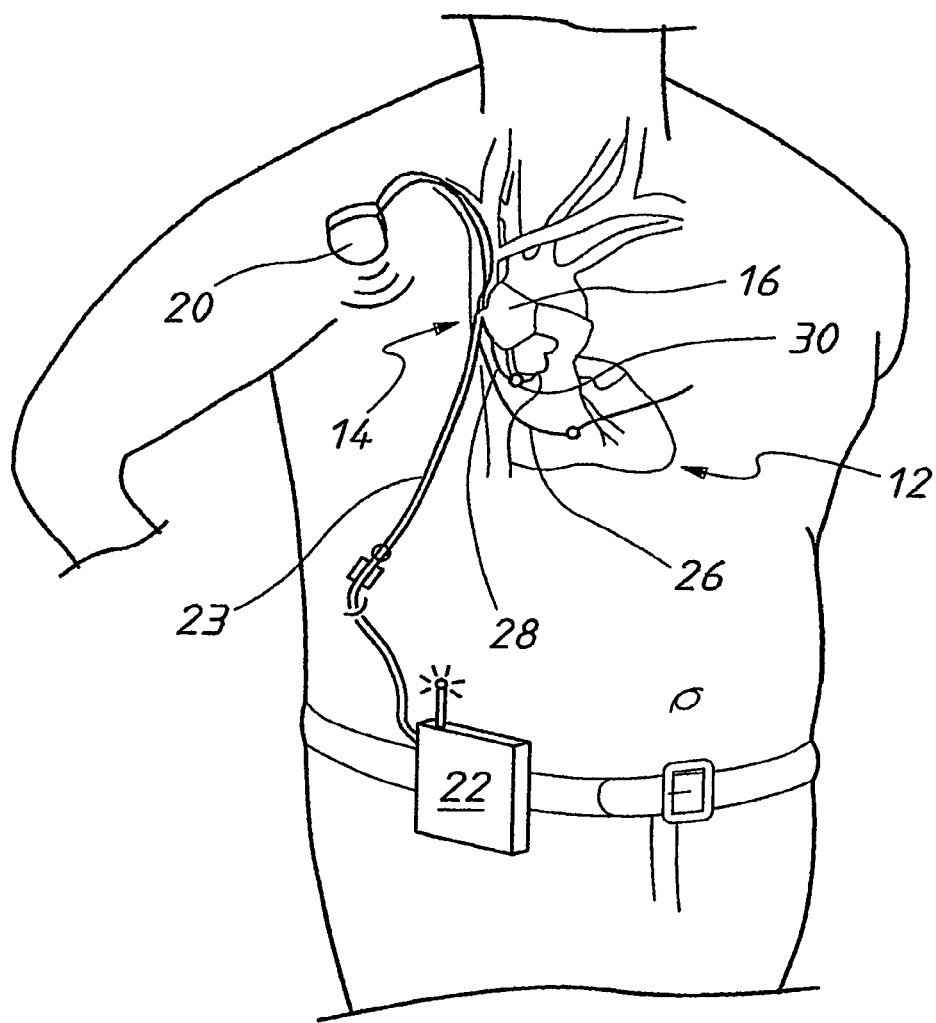
FIG. 2 is a cut away view of a patient with a heart assist device controlled in accordance with a second embodiment of the invention

A second embodiment of the invention will now be described with reference to FIG. 2, in which like features to the first embodiment will be indicated with like reference numerals. FIG. 2 shows a patient 10 with a heart 12. The output of the heart 12 is assisted by a pulsatile, partially implantable, heart assist device, indicated generally by the reference numeral 14. The heart assist device 14 has an aortic cuff 16 around the patient's ascending aorta. The cuff 16 is essentially the same as those disclosed in the Applicant's previously mentioned PCT Patent application. The cuff 16 is driven by an external pump and controller 22 via a percutaneous gas line 23. These types of pumps and controllers are well known to persons skilled in the art and will not be described in further detail herein. A battery (not shown) is also mounted within the casing of the pump and controller 22.

Also shown is the DSPT 20, which has an ECG channel connected to the sensing lead 26 and a PCG channel connected to the microphone lead 28. The DSPT transmits signals to the controller 22 of the heart assist device 14.

The DSPT ECG channel is connected, via the sensing lead 26, to the endocardial surface of the ventricle of the patient's heart 12 and the DSPT PCG channel is connected, via the microphone lead 28, to a microphone 30 implanted in close proximity to the aortic valve, also via the endocardium. These leads may be placed via the subclavian or jugular vein, and positioned in the right heart chamber, either the right atrium, right ventricle, or in the coronary sinus.

In operation, the DSPT 20 detects an R-wave (i.e. the R wave of the ventricle) through the ECG channel, then waits for a predetermined time (for example from 0-30 msec) before transmitting a signal to the controller 22 which in turn controls the pulsation of the heart assist device 14. It will be understood that, in the above configuration, the DSPT 20 will always issue the signal to the controller 22 and the controller may be programmable as to what action is taken when this signal is received. If desired, the DSPT 20 may issue the signal from the ECG channel immediately upon receiving the sensed signal in the ECG channel. In this case there would be a variable delay programmable into the controller 22 to ensure that the time at which the heart assist device 14 is actuated is correctly timed for that individual patient.

The DSPT 20 is implanted under the skin, preferably in the front of the shoulder, over the delto-pectoral region, or under the skin over the abdomen. This location makes it easy to locate a battery recharging coil or a programmer 'wand' (not shown).

Figure 3:
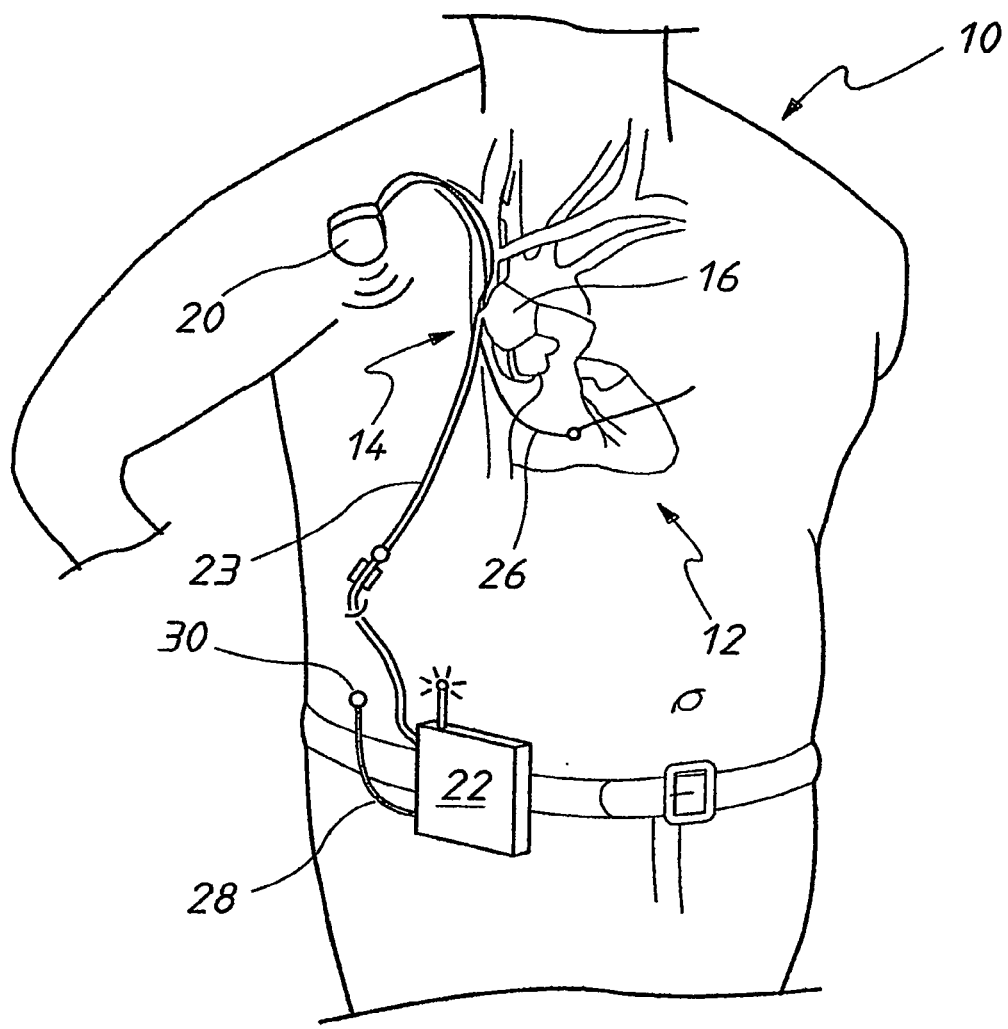
FIG. 3 is a cut away view of a patient with a heart assist device controlled in accordance with a third embodiment of the invention.

A third embodiment of the invention will now be described with reference to FIG. 3, in which like features to the second embodiment will be indicated with like reference numerals. The third embodiment is, and operates, very similar to the second embodiment except the microphone 30 detects heart sounds in the gas line 23 and the external controller 22 transmits corresponding signals to the PCG channel of the implanted DSPT 20.

A fourth embodiment of the invention will now be described with reference to FIG. 4, in which like features to the third embodiment will be indicated with like reference numerals. The fourth embodiment is very similar to the third embodiment except the heart assist device 14 is controlled using only heart sounds in the gas line 23 detected by the microphone 30. (i.e. no ECG signals are monitored). In this embodiment, the microphone 30 is positioned within an externally positioned housing 32 which also contains the pump and controller 22 and the DSPT 20. The microphone 30 is in direct communication with the gas line 23 which acts as a "stethoscope" transmitting sound from the heart 12 to the externally mounted microphone 30. In operation, the microphone 30 receives the S1 sound as the aortic valve opens and the DSPT transmits a signal indicative of that reception to the controller and pump 22. The heart assist device 14 is deflated on receipt of the DSPT signal. When the microphone 30 receives the S2 sound indicative of the aortic valve closing the DSPT signals the controller and pump 22 to reinflate the heart assist device 14. In this embodiment of the invention the DSPT may contain software to filter out sounds other than the S1 and S2 sounds or the system may be such that the pump is periodically stopped for a single heart beat to allow detection of the S1 and S2 sounds and the controller and pump 22 then operates for a predetermined time on the basis of the timing detected during the period that the pump was inoperative.

Figure 4:
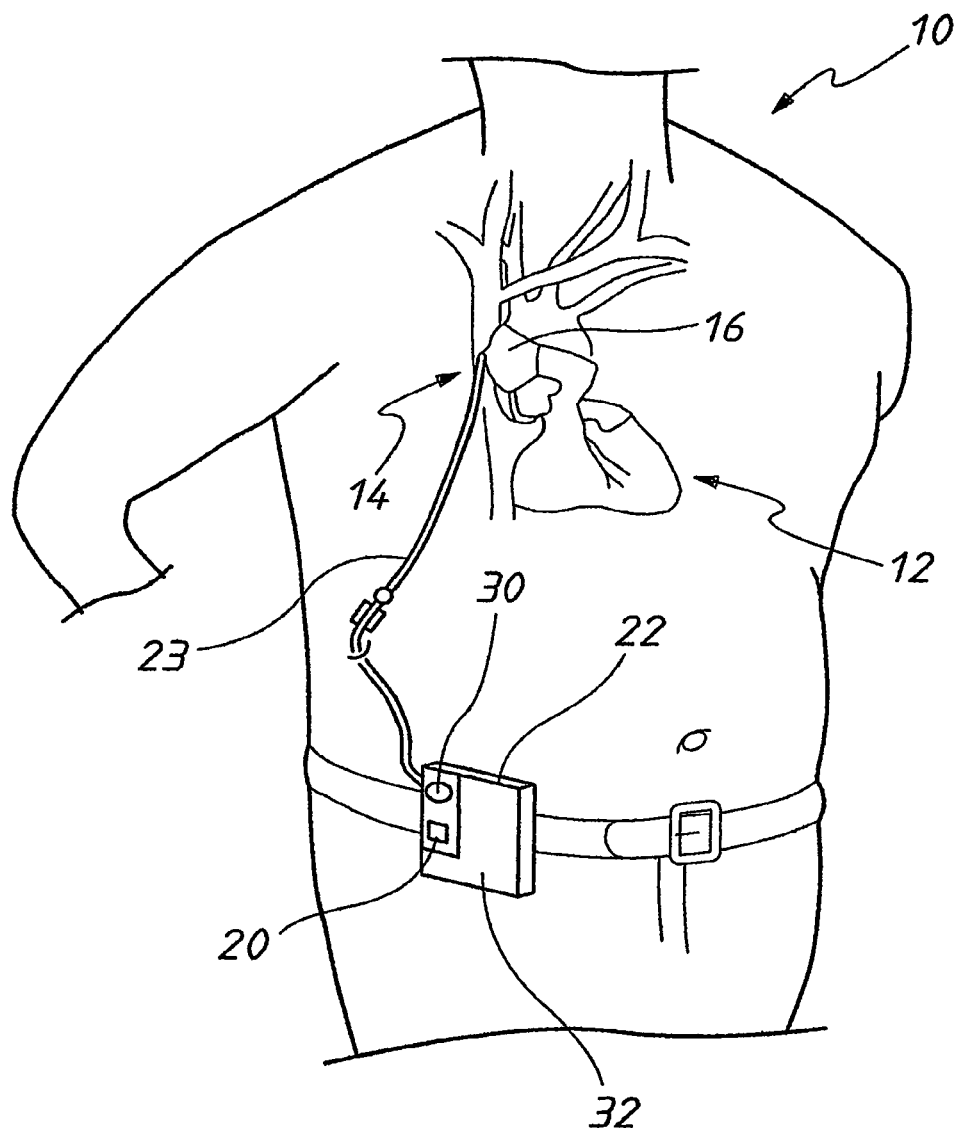
FIG. 4 is a cut away view of a patient with a heart assist device controlled in accordance with a fourth embodiment of the invention, in which an externally mounted housing containing the DSPT and the pump and controller is shown partially cut-away.

The arrangement shown in FIG. 4 may be altered by providing an ECG lead which extends from the heart 12 to the housing 32. In this case the DSPT will operate on the basis of the ECG detection of the R wave and on reception of the S2 sound. The ECG lead will preferably be disposed within the lumen of the gas line at the point of exit from the patient's body or be attached to the gas line. This means that there is only one point of percutaneous access into the patient. The ECG lead may also be brought out adjacent the gas line.

The detection of both R-wave and heart sounds dramatically improves the accuracy of timing the heart assist device accurately, from beat-to-beat, to events in the cardiac cycle such as the beginning of systole and diastole. Further, the signal transmission arrangement provides a cost effective and robust wireless telemetry system with minimal patient discomfort. Also, as the percutaneous gas line does not have to carry any internal leads, it can be made relatively smaller and more flexible to improve patient comfort.

It will be appreciated by the person skilled in the art that numerous variations and/or modifications may be made to the invention as shown in the specific embodiment without departing from the spirit or scope of the invention as broadly described. The present embodiment is therefore to be considered in all respects as illustrative and not restrictive.

For example, although epicardial leads are shown in FIG. 2, one lead could be endocardial and the other epicardial or visa versa.

What is claimed is:
1. A heart assist system, comprising:
 (a) a heart assist device comprising an inflatable cuff configured to apply pressure to blood in a blood vessel;
 (b) a pump configured to generate fluid pressure;
 (c) a fluid disposed within the inflatable cuff and the pump, the fluid configured to transfer the fluid pressure between the pump and the inflatable cuff;
 (d) a controller operably coupled to the pump; and
 (e) a phonocardiographic ("PCG") lead operably coupled to the controller, the PCG lead comprising a sound sensor configured to detect heart sounds, wherein at least a portion of the sound sensor is positioned in contact with the fluid, wherein the controller is configured to use the heart sounds to control the operation of the heart assist device.

2. The heart assist system of claim 1, wherein the blood vessel is an aorta, and further wherein the inflatable cuff is configured to apply the pressure to an exterior of the aorta.

3. The heart assist system of claim 1, wherein the inflatable cuff comprises a flexible membrane, wherein the flexible membrane is configured to apply the pressure to the blood in the blood vessel.

4. The heart assist system of claim 1, wherein the fluid is a liquid or a gas.

5. The heart assist system of claim 1, wherein the heart sounds comprise S1 and S2 sounds.

6. The heart assist system of claim 1, wherein the heart sounds comprise sounds created when an aortic valve of the heart closes.

7. The heart assist system of claim 1, wherein the sound sensor comprises a microphone.

8. A heart assist system, comprising:
(a) a pump configured to generate fluid pressure;
(b) an inflatable cuff operably coupled to the pump, the inflatable cuff configured to receive fluid pressure from the pump and apply pressure to blood in a blood vessel;
(c) a fluid disposed within the inflatable cuff and the pump, the fluid configured to transfer the fluid pressure between the pump and the inflatable cuff;
(d) a controller operably coupled to the pump;
(e) a digital signal processor and transmitter (DSPT) operably coupled to the controller, the DSPT comprising a PCG channel; and
(f) a PCG lead operably coupled to the PCG channel of the DSPT, the PCG lead comprising a sound sensor configured to detect heart sounds, wherein at least a portion of the sound sensor is positioned in contact with the fluid, wherein the DSPT is configured to transmit signals relating to the heart sounds to the controller, and further wherein the controller is configured to transmit actuation instructions to the pump based on the signals relating to the heart sounds from the DSPT.

9. The heart assist system of claim 8, wherein the sound sensor comprises a microphone.

10. The heart assist system of claim 8, wherein the DSPT is wirelessly coupled to the controller.

11. The heart assist system of claim 8, wherein the inflatable cuff comprises a flexible membrane, wherein the flexible membrane is configured to apply the pressure to the blood in the blood vessel.

12. The heart assist system of claim 8, wherein the fluid is a liquid or a gas.

13. A method of controlling a heart assist system, the method comprising:
positioning a PCG lead such that at least a portion of the PCG lead is positioned in contact with a fluid configured to transfer fluid pressure between a pump and an inflatable cuff;
detecting a heart sound with the PCG lead;
transmitting a signal relating to the heart sound to the controller; and
applying pressure to blood in a blood vessel with an inflatable cuff based on the heart sound.

14. The method of claim 13, further comprising transmitting an actuation signal from the controller to the pump based on at least one of the signals relating to the heart sound.

15. The method of claim 14, further comprising actuating the pump to generate fluid pressure based on the actuation signal.

16. The method of claim 15, further comprising transferring the fluid from the pump to the inflatable cuff as a result of the fluid pressure, whereby the inflatable cuff is inflated.

17. The method of claim 13, further comprising receiving the signals relating to the heart sound at a digital signal processor and transmitter (DSPT) and transmitting signals relating to the heart sound to the controller.

18. The method of claim 17, further comprising transmitting an actuation signal from the controller to the pump based on at least one of the signals relating to the heart sound from the DSPT.

* * * * *